United States Patent [19]

Takahashi et al.

[11] Patent Number: 5,773,005
[45] Date of Patent: Jun. 30, 1998

[54] PURIFIED FLAVONOID AND DITERPENE 5α-REDUCTASE INHIBITORS FROM THUJA ORIENTALIS FOR ANDROGEN-RELATED DISEASES

[76] Inventors: Hidehiko Takahashi, 15-26, Seijou 5-Chome; Susumu Hara; Rieko Matsui, both of c/o Kabushiki Kaisha Yakurigaku Chuo Kenkyusho, 15-4, Soshigaya 4-Chome, all of Setagaya-ku, Tokyo 157, Japan

[21] Appl. No.: 659,847

[22] Filed: Jun. 7, 1996

[30] Foreign Application Priority Data

Jun. 9, 1995 [JP] Japan .................................. 7-143504
Feb. 29, 1996 [JP] Japan .................................. 8-043029

[51] Int. Cl.⁶ .................. A61K 35/78; A61K 31/12; A61K 31/19; A61K 31/35
[52] U.S. Cl. .................. 424/195.1; 514/456; 514/557; 514/681; 514/729
[58] Field of Search .................. 424/195.1; 514/559, 514/880, 887, 456, 557, 681, 729; 536/128

[56] References Cited

FOREIGN PATENT DOCUMENTS 64-3125   1/1989   Japan .

OTHER PUBLICATIONS

Inoue et al. Terpenoids from the seed of Platycladus orientalis, Phytochemistry 24:1602–1604, 1985.

Muhammad et al. Further antibacterial diterpenes from the bark and leaves of *Juniperus procera* Hochst. ex Endl., Phytotheraphy Research, 9:584–588, 1995.

*Primary Examiner*—David M. Naff
*Assistant Examiner*—Janet M. Kerr
*Attorney, Agent, or Firm*—Gary M. Nath; Todd L. Juneau; Nath & Associates

[57] ABSTRACT

Strong 5αa-reductase inhibitors are extracted and fractionated from *Thuja orientalis* and other similar crude drugs or they may be purified as diterpenes in isolated form. The inhibitors are used either on their own or as active ingredients of therapeutics in the treatment of diseases caused by the overactivity of 5αa-reductase or the hypersecretion of androgens, such as male pattern baldness, androgenetic alopecia, hirsutism, acne, prostatomegaly and cancer of the prostate.

12 Claims, 2 Drawing Sheets

PURIFIED FLAVONOID AND DITERPENE 5α-REDUCTASE INHIBITORS FROM THUJA ORIENTALIS FOR ANDROGEN-RELATED DISEASES

BACKGROUND OF THE INVENTION

1. Field of the Invention

This invention relates to therapeutics of androgenetic diseases containing as active ingredients the nonsteroidal 5α-reductase inhibitors that have been obtained by fractioning the extracts of crude drugs including *Thuja orientalis, Fritillaria thunbergii*, etc. The fractionated extracts of these crude drugs are directly used as therapeutics or they may be chromatographically or otherwise isolated and fixed as diterpenes which provide more potent therapeutics. The therapeutics of the invention exhibit pronounced efficacy against androgenetic diseases such as male pattern baldness, androgenetic alopecia, hirsutism, acne, prostatomegaly, and cancer of the prostate.

2. Prior Art

Androgenetic diseases including acne, seborrhea, male pattern baldness, androgenetic alopecia, hirsutism, prostatomegaly and cancer of the prostate are induced by excessive production of 5α-dihydrotestosterone (DHT). Since the DHT is produced in a target organ by the reduction of androgens with 5α-reductase, active efforts are being made to develop therapeutics of androgenetic diseases that contain 5α-reductase inhibitors as active ingredients.

The 5α-reductase inhibitors are known to be available as steroids and nonsteroids. Potent nonsteroids are far from being suitable for clinical application. Some of the steroidal 5α-reductase inhibitors are at the advanced stage of commercialization but they cause the inevitable side effects of steroid hormones. Among the serious side effects caused by the steroid 5α-reductase inhibitors are infectious diseases, peptic ulcer, diabetes, mental disorders, hypertension, withdrawal syndrome and adrenal insufficiency; the inhibitors also cause mild side effects such as moon face, obesity, acne, hirsutism, emmenipathy, edema, insomnia, osteoporosity and thrombosis. Steroids can cause not only the intended clinical effects but also unwanted side effects, so they are prescribed judiciously by physicians who administer the minimum necessary dose for the clinical efficacy while taking cautions to keep the possible side effects to minimal levels.

Crude drugs which are of plant origin are mostly low in side effects but very few of them have been found to exhibit pronounced efficacy against androgenetic diseases.

Under the circumstances, the present inventors conducted extensive studies in order to develop nonsteroidal substances that were potent 5α-reductase inhibitors but which yet caused less side effects. The present inventors first discovered that a number of crude drugs had a 5α-reductase inhibiting action in their extracts; they then isolated highly active substances from the extracts, fixed them and made further research for clinical applications of those substances.

SUMMARY OF THE INVENTION

In the course of their study, the present inventors discovered that the 5α-reductase inhibitor contained in *Thuja orientalis* consisted of at least three components. Since two of the components (A and B) were contained in greater amounts and exhibited a higher inhibiting action than the other component (C), the present inventors first attempted to isolate A and B and analyze their structures. In a subsequent step, the inhibitor from component A was passed through a silica gel column and treated by preparative TLC on a thin layer coated with silver nitrate to isolate diterpenes; the inhibitor from component B was similarly treated to isolate flavonoids. The efficacy of the isolated diterpenes and flavonoids as inhibitors was examined by clinical tests. The inventors performed screening of the extracts of other crude drugs including *Fritillaria thunbergii, Trachylobium verrucosum, Chromolaena collina, Abies sibirca, Mikania alvimii*, and *Nicotiana raimondii* and successfully isolated diterpenes that were nonsteroidal compounds, that had a strong 5α-reductase inhibiting action and which yet caused limited side effects. The diterpenes and flavonoids could be used as therapeutics on their own or as active ingredients thereof in the treatment of diseases originating from the over activity of 5α-reductase or the hypersecretion of androgens. The present invention has been accomplished on the basis of these findings.

Disclosure of the Diterpenes

The diterpenes isolated in the present invention have a double bond in the 12- and 14-positions, with the double bond in the 12-position taking the configuration E. Such diterpenes have the following skeletal structures:

Specific examples of these compounds are listed below:
(E)-6-hydroxy-8(17),12,14-labdatrien-19-oic acid;
(E)-8(17),12,14-labdatrien-18-oic acid;
(E)-7-hydroxy-8(17),12,14-labdatrien-18-oic acid;
(E)-12,14-labdadien-3,8-diol;
(E)-12,14-labdadien-6,8-diol;
(E)-12,14-labdadien-7,8-diol;
(E)-12,14-labdadien-8,11-diol;
(E)-12,14-labdadien-8,18-diol;

(E)-12,14-labdadien-9,18-diol;
(E)-12,14-labdadien-1,8,18-triol;
(E)-12,14-labdadien-6,7,8-triol;
(E)-12,14-labdadien-6,8,18-triol;
(E)-12,14-labdadien-8-ol;
(E)-8(17),12,14-labdatriene;
(E)-7,12,14-labdatrien-6,17-diol;
(E)-8(17),12,14-labdatrien-3,19-diol;
(E)-8(17),12,14-labdatrien-18,19-diol;
(E)-8(17),12,14-labdatrien-3-ol;
(E)-8(17),12,14-labdatrien-7-ol; and
(E)-8(17),12,14-labdatrien-19-ol.

DESCRIPTION OF THE PREFERRED EMBODIMENTS

The present invention will now be described with reference to its preferred embodiments.

EXAMPLE 1

Substances capable of inhibiting 5α-reductase may be extracted and fractionated by the following procedure.

A powder of *Thuja orientalis* is mixed with about 5 volumes of n-hexane and the mixture is heated under reflux and filtered. The solvent in the filtrate is distilled off under vacuum and the residue is dissolved in 60% ethanol which is about twice the amount of the starting *Thuja orientalis* powder. The undissolved portion is filtered off and the solvent in the filtrate is distilled off under vacuum to yield a solid residue (component A).

The residue separated from the hexane extract is mixed with 60% ethanol which is about five times the amount of the starting *Thuja orientalis* powder and the mixture is heated under reflux and filtered. The solvent in the filtrate is distilled off under vacuum. To the residue, purified water is added in an amount about three times as much as the starting *Thuja orientalis* and the mixture is heated under reflux and filtered. The solvent in the residue is distilled off under vacuum to yield a solid residue (component B) whereas the filtrate is recovered as component C.

This is not the only procedure for extracting and fractionating components A, B and C and the n-hexane may be replaced by other solvents such as petroleum ether, petroleum benzine and benzene. The described procedure is efficient and achieves high yield.

A flowchart of this process is set forth below in Table 1.

TABLE 1

EXAMPLE 2

Figure 1:
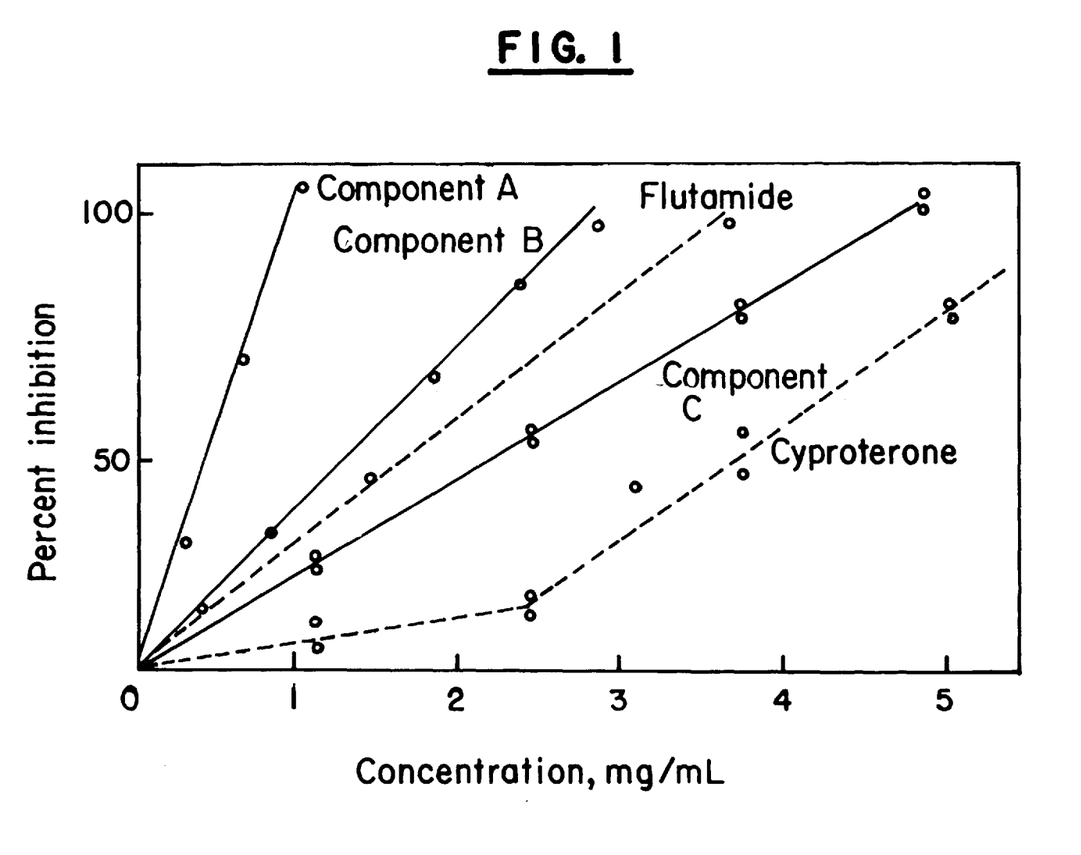
FIG. 1 is a graph comparing the extracts of *Thuja orientalis* (components A, B and C) with the prior art steroids flutamide and cyproterone in terms of their activity of inhibiting 5α-reductase.

The activities of components A, B and C in inhibiting the 5α-reductase prepared from the rat liver were measured. The method of preparing a crude 5α-reductase solution is shown in Table 2 and an outline of the method for assaying the enzymatic activity is shown in Table 3. Flutamide and cyproterone were used as positive controls. The results of the measurements are shown graphically in FIG. 1, from which one can see that components A and B are effective 5α-reductase inhibitors.

TABLE 2

```
Rat (SD, 7-wk old, females)
    |— anesthetize
    |— bleed with sucrose sol.
    |— remove liver
    |
  liver
    |— homogenize
    |— centrifuge at 10^4 g × 20 min.
    |
precipitate    supernate
                  |— centrifuge at 10^4 g × 20 min.
                  |
            precipitate    supernate
                              |— centrifuge at 10.5^4 g × 20 min.
                              |
                        precipitate    supernate
                                          |— suspend in sucrose sol.
                                       crude enzyme sol.
``` sucrose sol. consisted of 0.25 M sucrose and 1 mM EDTA Na$_2$.

TABLE 3

1) Reagent

|  | Amount of addition, ml | Final concentration, mmol/L |
|---|---|---|
| 0.28 mM Testosterone (10% MeOH sol.) | 0.25 | 0.07 |
| 50 mM Tris-HCl sol. (pH 7.0) | 0.1 | 5.0 |
| 50 mM NADPH sol. | 0.1 | 5.0 |
| Sample (in 60% EOH) | 0.05 | — |
| Crude enzyme sol. | 0.025 | — |
| Purified water | 0.475 | — |
| To make | 1.0 | |
| Extractant: dichloromethane | 2.0 | |

TABLE 3-continued

2) Method

EXAMPLE 3

Components A and B were isolated in pure form and analyzed for structure. Outlines of the methods for isolation are shown in Tables 4 and 5.

On the basis of $^1$H-NMR, $^{13}$C-NMR, mass and IR spectral analyses, the active principle in component A as a 5α-reductase inhibitor was estimated to be a terpenoid and that in component B as a flavonoid.

TABLE 4

TABLE 5

EXAMPLE 4

The 5α-reductase inhibitors extracted from *Thuja orientalis* were examined for their efficacy against male pattern baldness in stage V. The test samples were components A, B and C, as well as the terpenoid isolated from component A and the (iso)scutellarein isolated from component B, which were each dissolved at a concentration of 1% in 50% alcohol. These samples were daily applied on a twice-a-day basis for a period of 4 months to the bald heads of 27–45 year old male volunteers in five groups each consisting of 5 cases. The test samples had no significant difference in therapeutic effects and all of them caused pronounced regrowth of hair. The extracts of *Thuja orientalis* were also examined for their efficacy against androgenic alopecia in women and there was found no significant difference by sex.

EXAMPLE 5

Male hirsute volunteers (aged 25–40) had the hair in both inferior limbs depilated with wax in an area of 5 cm$^2$. To the depilated area of one inferior limb, component A, B, the terpenoid isolated from component A or the (iso)scutellarein isolated from component B that were dissolved at a concentration of 1% in 50% alcohol was applied. The depilated area of the other inferior limb was set aside as a control section and treated with 50% alcohol alone. Each volunteer group consisted of 5 cases. Regrowth of hair was significantly suppressed in the test sections as compared to the control section. When the experiment ended 3 months later, the control section was indistinguishable from the surrounding area but the regrowth of hair in the test sections was barely recognizable. There was also found no significant difference in efficacy among the test samples.

EXAMPLE 6

Patients in their twenties suffering from acne were divided into four groups, each consisting of 3 males and 3 females. Component A, B, the terpenoid isolated from component A or the (iso)scutellarein isolated from component B which were each dissolved in 1,3-butylene glycol at a concentration of 1% was applied to the diseased area of each person's face after washing with takallophene soap. The application was done daily on a twice-a-day basis and continued for a period of 2 months. The acne in each patient was diagnosed as being moderate and a mixture of comedones (primarily whiteheads), papules and pustules.

The therapeutic effects of the test samples were obvious; 60% of the treated cases were almost cured; 30% was half cured; and 10% showed a 30% reduction in severity. There was found no significant difference in efficacy among the test samples; the difference by sex was also insignificant.

EXAMPLE 7

Among the diterpenoids to be used in the invention, (E)-8 (17),12,14-labdatrien-18-oic acid may be extracted and isolated in pure form by the following procedure.

A powder of *Thuja orientalis* is mixed with about 5 volumes of n-hexane and the mixture is heated under reflux and filtered. The solvent in the filtrate is distilled off under vacuum and the residue is dissolved in 60% ethanol which is about twice the amount of the starting *Thuja orientalis* powder. The undissolved portion is filtered off and the solvent in the filtrate is distilled off under vacuum to yield a solid residue (component A).

This is not the sole procedure for extracting and fractionating component A and the n-hexane may be replaced by other solvents such as petroleum ether, petroleum benzine and benzene. The described procedure is efficient and achieves high yield.

Thus obtained component A is passed through an open silica gel column with a mixture of n-hexane and ethyl acetate being used as a developing solvent system. Following TLC on a thin layer coated with silver nitrate, the active spot containing the desired inhibitor was scraped and passed again through an open silica gel column to prepare a pure sample.

A flowchart of this process is set forth below in Table 1'.

TABLE 1'

EXAMPLE 8

A substance having the 5α-reductase inhibiting activity was isolated from component A as one having the most intense uv absorption and the sturcture of the thus isolated substance was characterized.

When a $^1$H NMR spectrum was taken, similar quartet peaks were found at δ values of 6.8 and 6.3 whereas similar triplet peaks occurred at δ values of 5.4 and 5.3. Since the integral was 1 at δ=6.3 and 5.4 and 0.7 at δ=6.8 and 5.3, two substances of similar structures having respective triplet and quartet peaks in pairs were assumed to be present in component A. To varify this assumption, component A was subjected to preparative TLC on a thin layer coated with silver nitrate, whereby the two substances could be isolated.

These substances were characterized for their structures by measuring $^1$H and $^{13}$C NMR spectra, mass spectrum, ir absorption spectrum, uv absorption spectrum and optical rotation; as a result, both substances were estimated to be 8(17), 12,14-labdatrien-19-oic acid having the labdane skeleton. In order to identify their stereostructures, a NOESY plot was taken for the protons in the $^1$H NMR spectrum; in one compound, correlationship was found between the 14-position and each of the 15- and 12-positions and in the other compound, correlationship was found between the 14-position and each of the 15- and 16-positions; hence, the two compounds were estimated to be of an (E)- and a (Z)-form, respectively. Similarly, an absorption occurred at 990 cm.$^{-1}$ and 770 cm.$^{-1}$ in the ir spectrum. Hence, the two compounds were determined to be (E)- and (Z)-8(17),12, 14-labdatrien-19-oic acid.

A crude enzyme solution for assaying the 5α-reductase inhibiting action was prepared according to the procedure already set forth in Table 2.

Using the thus prepared crude enzyme solution, the 5α-reductase inhibiting action was assayed by the method set forth in Table 7 under 2).

TABLE 7

1) Reaction fluid

| Ingredient | Amount of addition, ml | Final concentration, mmol/L |
|---|---|---|
| 0.28 mM testosterone (in 10% MeOH) | 0.25 | 0.07 |
| 50 mM Tris-HCl buffer solution (pH 7.0) | 0.10 | 5.0 |
| 50 mM NaPH solution | 0.25 | 5.0 |
| Sample (in 60% EOH) | 0.25 | — |
| Crude enzyme solution | 0.025 | — |
| Purified water | 0.325 | — |
| To make | 1.0 | |

2) Assay method

Reaction fluid
|
Incubate at 37° C. × 20 min.
|
— Extract testosterone with dichloromethane
|
Stir 30 min.
|
Centrifuge at 3000 rpm × 10 min.
|
┌──────────────┐
Dichloromethane     Aqueous layer
layer
|
Measure absorbances $A_0$ and $A_{20}$ at 240 nm

*For measuring $A_0$, the reaction fluid and dichloromethane were charged simultaneously and the mixture was immediately stirred without incubation. For measuring $A_0$ and $A_{20}$ on the control, the sample was subjected to reaction in 60% ethanol.

Figure 2:
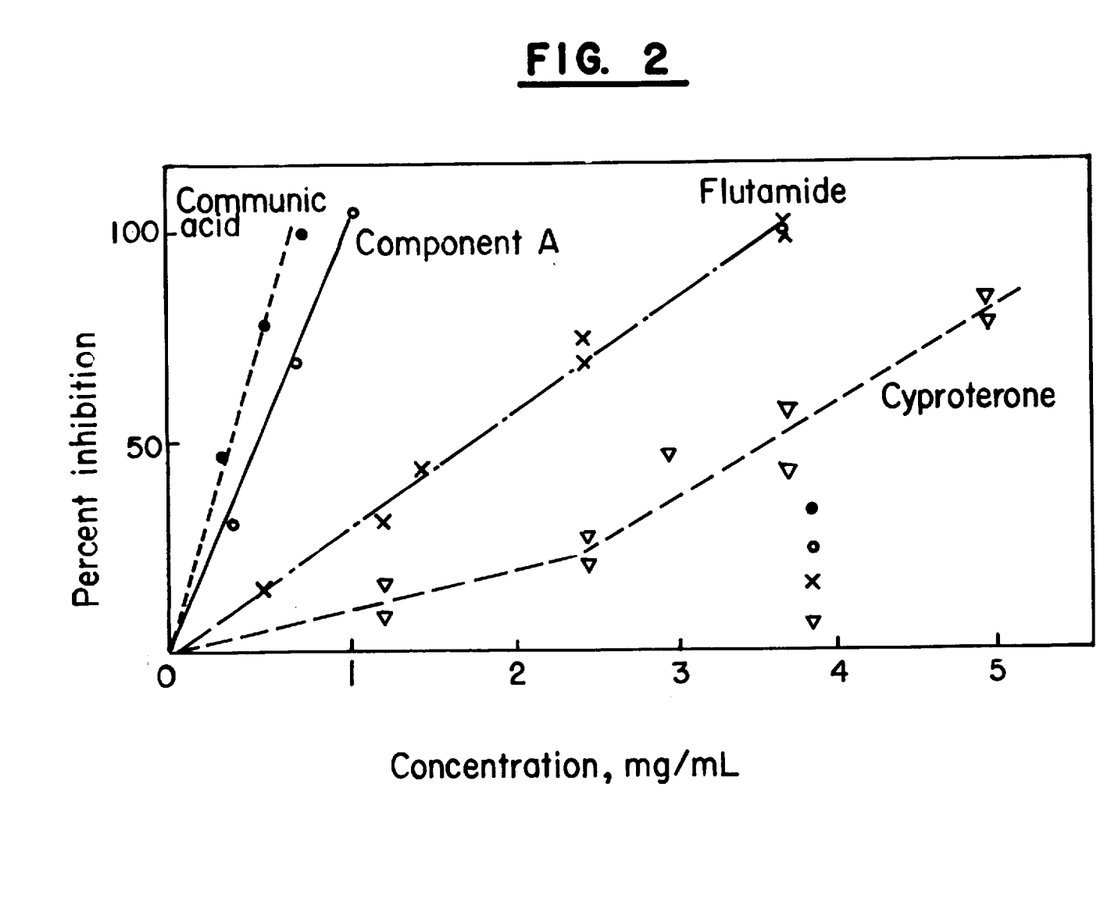
FIG. 2 is a graph comparing the extract (component A) of *Thuja orientalis*, the trans-communic acid isolated from component A and the prior art steroids flutamide and cyproterone in terms of their activity of inhibiting 5α-reductase in vitro.

The extract of *Thuja orientalis* (component A), the trans-communic acid isolated from component A, flutamide and cyproterone were measured for their activity in inhibiting 5α-reductase in vitro and the results are shown graphically in FIG. 2. The percent inhibition of 5α-reductase was calculated by:

$$\left(1 - \frac{\exp. A0 - A20}{\text{cont.} A0 - A20}\right) \times 100$$

EXAMPLE 9

Patients in their twenties who were suffering from acne were divided into five groups each consisting of 3 males and 3 females and treated with a lotion of the following formula prepared in accordance with the invention.

TABLE 8

| Ethanol | 50% |
|---|---|
| 1,3-Butylene glycol | 20% |
| HCO-60 | 3% |

TABLE 8-continued

| Diterpene | 1% |
|---|---|
| Purified water | 26% |

The lotion was applied to the diseased part of a patient's face after washing with takallophene soap and the treatment was conducted daily on a twice-a-day basis for a period of 2 months. The acne in each patient was diagnosed as being moderate and a mixture of comedones (primarily whiteheads), papules and pustules.

The results were evaluated by the following criteria: 3, cured completely; 2, half cured; 1, cured 30%; 0, not cured. The highest score was 18 and the lowest score was 0.

TABLE 9

| Diterpenoid | Score | |
|---|---|---|
| | 1 mol | 2 mo. |
| Sample I | 8 | 18 |
| Sample II | 10 | 18 |
| Sample III | 9 | 18 |
| Flutamide | 4 | 8 |
| Water | 0 | 0 |

Sample I: (E)-8(17),12,14-labdatrien-19-oic acid
Sample II: (E)-8(17),12,14-labdatriene
Sample III: (E)-8(17),12,14-labdatrien-19-ol The therapeutic effects of the three diterpenoids under test were obvious and there was no significant difference in efficacy among them. There was also found no significant difference by sex.

Another formula of acne curative may be as follows.

TABLE 10

| Ingredient | Percent by weight |
|---|---|
| Trans-diterpene | 0.01–1.0 |
| Synthetic silica alumina | 1.0–3.0 |
| Takallophene | |
| Urea | 2.0 |
| Sodium salicylate | 0.2 |
| Solvent | to make 100 |

When the diterpene and takapherone were incorporated at respective concentrations of 0.1% and 3%, the formula as applied to patients suffering from moderate acne (aged 19–51; 13 males and 44 females) gave the following result after 4 months of application: 5 cases cured completely and 52 cases showed a pronounced effect as evidenced by the decrease in the number of eruptions to one third or less.

EXAMPLE 10

Diterpenes of the invention were evaluated for their therapeutic effects on male pattern baldness in stage V. The curatives were prepared in accordance with the formula set forth in Table 11.

TABLE 11

| Ethanol | 50% |
|---|---|
| Propylene glycol | 10% |
| HCO-60 | 3% |

TABLE 11-continued

| Diterpene | 1% |
|---|---|
| Purified water | 36% |

The curatives were applied to the bald area of male volunteers (aged 27–45) in five groups each consisting of 5 cases. The application was done daily on a twice-a-day basis and continued for 6 months. The therapeutic efficacy was evaluated by the following criteria based on the decrease in the area of the parietal alopecic lesion and the density of regrowing hairs: 10 (alopecic area decreased to ⅕ or less and hair density increased by ⅔ or more); 7 (alopecic area decreased to ⅓ or less and hair density increased by ⅓ or more); 4 (alopecic area decreased to ½ or less and hair density increased by ⅕ or more); 2 (alopecic area decreased by 20% and hair density increased by 10% or more); 1 (alopecic area hardly changed but hair density increased definitely); 0 (no change at all).

TABLE 12

| Diterpeniod | Score | | | | |
|---|---|---|---|---|---|
| | 0 mo. | 1 mo. | 2 mo. | 4 mo. | 6 mo. |
| Sample I | 0 | 1 | 4 | 7 | 10 |
| Sample II | 0 | 1 | 4 | 7 | 10 |
| Sample III | 0 | 0 | 4 | 7 | 10 |
| Flutamide | 0 | 1 | 2 | 2 | 4 |
| Water | 0 | 0 | 0 | 0 | 0 |

Sample I: (E)-8(17),12,14-labdatrien-19-oic acid
Sample II: (E)-8(17),12,14-labdatriene
Sample III: (E)-8(17),12,14-labdatrien-19-ol The three diterpenes under test had no significant differences in therapeutic efficacy and they all proved to be definitely effective in curing male pattern baldness.

EXAMPLE 13

An experiment was conducted on 5 hirsute male volunteers aged 25–48. The center of each straight leg was depilated with wax to create a lesion about 2 cm wide and 3 cm long. The depilated lesion on one inferior limb was treated with 50% ethanol and the lesion on the other inferior limb was treated with 0.1% trans-communic acid dissolved in 50% ethanol. The application was done daily on a twice-a-day basis for 3 consecutive months. The results were as follows.

TABLE 13

| Case | Control section | Test section |
|---|---|---|
| A | Regrowth of hair in the depilated area was indistinguishable from the hair density in the surrounding area. | No regrowth of hair in the depilated lesion |
| B | Regrowth of hair in the depilated area was indistinguishable from the hair density in the surrounding area. | No regrowth of hair in the depilated lesion |
| C | Regrowth of hair in the depilated area was indistinguishable from the hair density in the surrounding area. | Regrowth of a few hair |

TABLE 13-continued

| Case | Control section | Test section |
|---|---|---|
| D | Regrowth of hair in the depilated area was indistinguishable from the hair density in the surrounding area. | No regrowth of hair |
| E | Regrowth of hair in the depilated area was indistinguishable from the hair density in the surrounding area. | No regrowth of hair |

EXAMPLE 14

Five women (aged 20–35) suffering from idiopathic hirtuism were treated with 0.1% trans-communic acid in 50% ethanol that was applied daily to a wax depilated area of the right forearm on a twice-a-day basis. Depilation was repeated every other month until the end of the experiment. The overall results of the experiment are shown in Table 14 below.

TABLE 14

| | First measurement (before treatment) | | Sixth measurement | |
|---|---|---|---|---|
| Case | Hair density | Hair length, mm | Hair density | Hair length, mm |
| A | thick | peaked at ca. 10 mm | sparse | peaked at ca. 10 mm |
| B | thick | peaked at ca. 6 mm | a few | ca. 1 mm |
| C | thick | peaked at ca. 10 mm | sparse | peaked at ca. 3 mm |
| D | thick | peaked at ca. 8 mm | a few | ca. 2 mm |
| E | thick | peaked at ca. 7 mm | a few | ca. 1 mm |

Measurements were conducted on the hairs attached to the cloth used for wax depilation.

EXAMPLE 15

Seven-week old BALB/CA-nu/nu mice were transplanted with androgen-dependent human prostatic cancer strain HONDA beneath the dorsal skin and 6-week old BALB/CA-nu/nu mice were transplanted with androgen-dependent rat prostatic cancer strain R3327-G beneath the dorsal skin. When the respective tumors grew to a specified size, the animals were divided into test and control groups. The test groups were administered with suspensions of trans-communic acid and flutamide in 0.5% CMC. The control groups were administered with 0.5% CMC alone. The drugs and the vehicle were administered perorally via an oral probe. The administration was repeated daily for 28 consecutive days on a once-a-day basis. The tumor volume ($mm^3$) was calculated by the formula of major axis (mm) × the square of minor axis ($mm^2$)/2. The drugs were rated as "effective" when they could control the growth of tumors to such a degree that the tumor volume was no more than half the volume of tumors in the control groups and when the difference was found to be statistically significant in the student's t test ($p<0.05$).

Strain HONDA decreased in size when the mice carrying that cancer were castrated. Trans-communic acid could control the growth of this cancer significantly in a dose-dependent manner. The positive control flutamide was also effective in tumor control but its efficacy was considerably weaker than that of trans-communic acid and the tumor size of the group administered with 20 mg/kg of trans-communic acid was almost comparable to that of the group administered with 200 mg/kg of flutamide.

The growth of cancer strain R3327-G was not controlled in castrated mice when they were administered 25 mg of testosterone enanthat per head concurrently with the cancer transplantation. Even in such mice, trans-communic acid could effectively control the growth of cancer in a dose-dependent manner and its efficacy was considerably stronger than that of flutamide.

We claim:

1. A non-steroidal inhibitor of 5α-reductase extracted from *Thuja orientalis* wherein the inhibitor is selected from the group consisting of purified (iso)scutellarein and a purified diterpene that has a double bond in the 12- and 14- positions, with the double bond in the 12- position taking the configuration E.

2. The inhibitor of claim 1, wherein the diterpene has a labdane skeleton.

3. The inhibitor of claim 1, wherein the diterpene is selected from the group consisting of:

(E)-6-hydroxy-8(17),12,14-labdatrien-19-oic acid;
(E)-8(17),12,14-labdatrien-18-oic acid;
(E)-7-hydroxy-8(17),12,14-labdatrien-18-oic acid;
(E)-12,14-labdadien-3,8-diol;
(E)-12,14-labdadien-6,8-diol;
(E)-12,14-labdadien-7,8-diol;
(E)-12,14-labdadien-8,11-diol;
(E)-12,14-labdadien-8,18-diol;
(E)-12,14-labdadien-9,18-diol;
(E)-12,14-labdadien-1,8,18-triol;
(E)-12,14-labdadien-6,7,8-triol;
(E)-12,14-labdadien-6,8,18-triol;
(E)-12,14-labdadien-8-ol;
(E)-8(17),12,14-labdatriene;
(E)-7,12,14-labdatrien-6,17-diol;
(E)-8(17),12,14-labdatrien-3,19-diol;
(E)-8(17),12,14-labdatrien-18,19-diol;
(E)-8(17),12,14-labdatrien-3-ol;
(E)-8(17),12,14-labdatrien-7-ol; and
(E)-8(17),12,14-labdatrien-19-ol.

4. A method of treating androgenetic diseases selected from the group consisting of acne, seborrhea, male pattern baldness, androgenetic alopecia, hirsutism, prostatomegaly, and cancer of the prostate, which comprises administering a therapeutically effective amount of the inhibitor of claim 1 to an animal.

5. A method of inhibiting the activity of 5α-reductase in an animal, which comprises administering a therapeutically effective amount of the inhibitor of claim 1.

6. A method for regrowth of hair in an animal, which comprises administering a therapeutically effective amount of the inhibitor of claim 1.

7. A method of treating acne in an animal, which comprises administering a therapeutically effective amount of the inhibitor of claim 1.

8. A method of treating male pattern baldness in an animal, which comprises administering a therapeutically effective amount of the inhibitor of claim 1.

9. A method of treating hirsutism in an animal, which comprises administering a therapeutically effective amount of the inhibitor of claim 1.

10. A method of treating idiopathic hirsutism in an animal, which comprises administering a therapeutically effective amount of the inhibitor of claim 1.

11. A method of treating androgenetic diseases caused by the overactivity of 5α-reductase in an animal, which comprises administering a therapeutically effective amount of the inhibitor of claim 1.

12. A method of treating androgen dependent prostate cancer in an animal, which comprises administering a therapeutically effective amount of the inhibitor of claim 1.

* * * * *